United States Patent [19]

Oldham et al.

[11] Patent Number: 4,736,755

[45] Date of Patent: Apr. 12, 1988

[54] METHOD OF LOADING NICOTINE INTO POROUS POLYMERIC ITEMS

[75] Inventors: Ronald G. Oldham; Michael P. Ellis, both of San Antonio, Tex.; Ira D. Hill, Locust, N.J.

[73] Assignee: Advanced Tobacco Products, San Antonio, Tex.

[21] Appl. No.: 817,440

[22] Filed: Jan. 8, 1986

Related U.S. Application Data

[63] Continuation-in-part of Ser. No. 773,409, Sep. 6, 1985, which is a continuation-in-part of Ser. No. 738,120, May 24, 1985.

[51] Int. Cl.$^4$ .......................... A24D 1/04; A24D 3/02
[52] U.S. Cl. ..................................... 131/270; 131/332; 493/49
[58] Field of Search .................. 131/332, 270; 493/49

[56] References Cited

U.S. PATENT DOCUMENTS 3,595,245  7/1971  Buntin ................................. 131/332
3,880,173  4/1975  Hill ..................................... 131/332

Primary Examiner—V. Millin
Attorney, Agent, or Firm—Arnold, White & Durkee

[57] ABSTRACT

A method of loading nicotine into porous polymeric items consisting essentially of a polyolefin. The method comprises contacting the items with nicotine or nicotine dissolved in a carrier. The polyolefin item, preferably polyethylene or polypropylene, may be loaded with nicotine by several variations on the basic method. The items may be emplaced in a vessel with nicotine and the vessel then closed for a period of time prior to removal of said items.

A preferred method of producing porous polyethylene items loaded with nicotine comprises first emplacing porous polyethylene items in a vessel. A solution comprising between about 1% nicotine and about 10% nicotine and a solvent for nicotine demonstrating an adherence for polyethylene surfaces is prepared. A quantity of this solution sufficient to contact at least a majority of the polyethylene items is added to the vessel. Excess solution is then drained from the items and the solvent evaporated from the items to produce porous polyethylene items loaded with nicotine.

35 Claims, No Drawings

METHOD OF LOADING NICOTINE INTO POROUS POLYMERIC ITEMS

This is a continuation-in-part of co-pending U.S. Ser. No. 773,409 filed Sept. 6, 1985 which, in turn, is a continuation-in-part of co-pending U.S. patent application Ser. No. 738,120, filed May 24, 1985, both assigned to the assignee of the present invention.

BACKGROUND OF THE INVENTION

This invention relates to methods of loading porous polyolefinic items with nicotine. These nicotine-loaded porous polyolefinic items are adapted for usage in nicotine dispensers simulating in appearance, for example, cigarettes. The polyolefinic items absorb nicotine in a manner as yet incompletely defined but characterized by a reversibility, i.e., absorbed nicotine may be liberated as a vapor or gas.

Previous U.S. patents, for example U.S. Pat. No. 3,280,823, described a tobacco smoke filter comprising nicotine held in ionic bondage to an ion-exchange resin. The use of polyolefins to absorptively and reversibly retain nicotine has not been described except in the copending U.S. patent application Ser. No. 738,120.

SUMMARY OF THE INVENTION

A method of loading nicotine into porous polymeric items consisting essentially of a polyolefin or polyolefindiene. The method comprises contacting the items with nicotine or nicotine dissolved in a carrier. The polymeric item, preferably consisting essentially of polyethylene or polypropylene, may be loaded with nicotine by several variations on the basic method. The items may, for example, be emplaced in a vessel with nicotine and the vessel then closed for a period of time prior to removal of said items.

A preferred method of producing porous polyethylene items loaded with nicotine comprises first emplacing porous polyethylene items in a vessel. A solution comprising between about 1% nicotine and about 10% nicotine by weight and a solvent for nicotine demonstrating an adherence for polyethylene surfaces is prepared. A quantity of this solution sufficient to contact at least a majority of the polyethylene items is added to the vessel. Excess solution is then drained from the items and the solvent evaporated from the items to produce porous polyethylene items loaded with nicotine.

DESCRIPTION OF PREFERRED EMBODIMENTS

The porous polymeric items of the present invention may also be termed porous polymeric plugs or merely porous plugs because of the short cylindrical shape preferred to be interposed in a cigarette-shaped tube, such terms being viewed as equivalent herein.

A nicotine-bearing mixture or nicotine itself may be dispersed in and then dispensed from a porous polymeric plug. It has been found that a number of substances may be advantageously provided in the nicotine or nicotine mixture which is placed in the porous plug of the present invention. Nicotine (d), nicotine (l), nicotine (dl) and possibly mixtures containing nicotine salts may all be used to advantage as the nicotine or nicotine in nicotine-bearing mixture of the present invention to provide nicotine vapors which are inhaled by the user. A product obtained commercially from Eastman Company, Stock No. 1242, having 98% nicotine (l), has been used and found to perform with satisfactory results. The term "nicotine" as used herein, unless otherwise defined, indicates usage of Eastman Company nicotine or that from any numerous commercial sources. Commercial nicotine is preferably distilled under vacuum to provide high purity nicotine for use in the present invention.

Any number of nicotine-bearing mixtures are usable for emplacement in the porous plugs of the present invention. The specific nicotine-bearing mixture being used in a particular embodiment of the present invention is dependent upon the specific substances desired to be present in the loaded porous plug. In preferred embodiments of this invention, a number of other materials have been found to provide advantageous results when added to the nicotine bearing mixture. The commercial nicotine which is available in the marketplace is entirely a byproduct of the tobacco industry. Extraction and purification procedures are generally well-known in the tobacco industry. Additives to the nicotine being incorporated into porous plugs may include flavorants such as menthol, methyl salicylate or commercially available tobacco flavorings, for example.

Anti-oxidants such as butylated hydroxytoluene, butylated hydroxyanisole, propyl gallate or tertary butyl hydroxyquinone may also be added to the nicotine before or after impregnation into a porous plug. Such antioxidants, for example, may be used to stabilize nicotine for a longer shelf life.

For the purpose of the present invention polyolefins are reversibly absorptive to nicotine so that nicotine is absorbed and releaseable therefrom. However, it is also important that the material be sufficiently absorbent of releasable nicotine to hold enough nicotine so that at least about 1 microgram is dispensed in response to each 35 cc puff of air drawn through a nicotine-loaded porous plug. The porous plug is typically of a material generically described as an olefinic polymer. More specifically, the polyolefin is preferably polyethylene or polypropylene but are thought also to be any polyolefin or polyolefindiene such as polybutadiene, poly-1-butene, polyisobutylene, polyisoprene, poly-4-methyl pentene, or combinations thereof, for example. Of particular preference is formulating the porous plug of the present invention is a high density polyethylene. Although amorphous rather than highly crytalline polyethylene appears to have a greater nicotine-absorptive capacity, porous plugs are more readily produced from high density polyethylene which has adequate capacity for reversible nicotine absorption. The porous plug may be produced mechanically or may also be a shaped mass of filaments.

Polymeric substances such as polystyrene and polycarbonate are dissolved by nicotine and are thus not usable as the porous plugs of the present invention. Polymers containing halogens or nitrogen or sulfur, although they may be found to have the desired reversible nicotine absorptivity are not preferred because of their potential emission of noxious fumes upon accidental ignition.

Loading porous polyolefin or polyolefindiene items or plugs with nicotine may be accomplished in several ways. For example, said items may be loaded with nicotine by contacting them with nicotine in its liquid or vapor form. In a simple aspect, a droplet of nicotine may be emplaced on a polyolefin item and be absorbed thereinto. By simply contacting the items with nicotine, their loading is assured.

In a more sophisticated and more preferred manner, the porous polyolefin or polyolefindiene item may be emplaced in a closable vessel. When nicotine vapor or nicotine liquid or both are also in the vessel, the vessel may be closed and the absorption of nicotine by the items permitted to ensue to a desired extent. The items loaded with nicotine may then be removed from the vessel.

An even more preferable method of producing porous polyolefin or polyolefindiene items loaded with nicotine comprises contacting these items with a solution of nicotine and a solvent with adherence for a polyolefin or polyolefindiene surface. The solvent has four important characteristics: it must dissolve nicotine; it must not dissolve polyolefins or polyolefindienes, it must adhere to a polyolefin or polyolefindiene surface; and it must have a boiling point less than that of nicotine which is about 247° C. at 745 mm Hg. If the addition of flavorants and/or antioxidants are to be done via this solvent, they should, of course, dissolve therein. The solvent, since it is destined to be at least largely removed from the items, once they have absorbed nicotine, should most preferably have a boiling point less than about 200° C. This difference in boiling points permitting an evaporative removal of solvent, for example, by placement in rotary evaporator.

By the language "adhere to a (particular) surface", or "adherence to a polyolefin, polyethylene, etc. surface", as used herein, is meant to indicate an interaction most often characterized as "wetability". For example, water wets glass but not plastics and oils wet plastics but not glass. This adherence or "wetting" characteristic is frequently measured by the sloping angles demonstrated by a droplet of a particular liquid on a particular surface. As used herein, adherence to a surface means that the solvent "wets" that surface. With porous items having large internalized surface areas, such "wetting" is desired to carry dissolved nicotine to maximal surface contact, particularly upon largely internalized surfaces.

As a further example, pure polyethylene is not wetted by water but is wetted by alkyl alcohols with between one and eight carbon atoms, paraffins or olefins with between three and eight carbon atoms, ketones with between three and eight carbon atoms, aliphatic ethers with between two and six carbon atoms, aliphatic esters with between four and six carbon atoms, liquid $CO_2$, or halogenated paraffins having between one and six carbon atoms. Such fluids or solvents described above do not provide an exhaustive list of fluids or solvents contemplated by those skilled in the art to have the properties necessary for function in the present invention. Supercritical fluids contemplated to be useful (organic fluids or inorganic fluids such as $CO_2$, $N_2$, or $NH_3$ for example) having greatly enhanced ability to absorb numerous substances and yet be unable to dissolve polyolefins and to be relatively easily "flashed" or evaporated away. Particularly when more traditional organic solvents are used to dissolve nicotine, it is preferred that they be anhydrous. Nicotine is very water soluble and water slows absorption of nicotine into polyolefins. Preferred so events also leave no noticeable taste or odor residue after evaporation.

In a preferred method of the present invention, porous polyolefin or polyolefindiene plugs are covered with a fluid solvent containing from about 1% to about 10% nicotine by weight. After the plugs have filled by spontaneous capillary action, the excess solution may be drained off. The wetted plugs are then exposed to ambient air to permit solvent evaporation therefrom. These wetted plugs may be placed in a vacuum (for example, a rotary vacuum drier) for the application of vacuum, warmth and agitation to facilitate solvent removal. Porous polyolefin or polyolefindiene items loaded with nicotine may thus be produced.

A preferred method for enhancing the uniformity and reproducability of nicotine loading into porous nicotine-absorbent polymeric plugs involves the concept of "void volume" and the use of solvent-nicotine solutions. The term "void volume" as used herein corresponds to the amount of "wetting" solvent which will adhere to a porous plug, particularly in its porous interstices. The porosity of a porous plug may be varied by many means known to those skilled in the related arts.

Void volume was calculated by the determination of plug weight gain after a particular exposure to a wetting solvent of low volatility. This exposure most preferably was substantially the same as the planned plug exposure to a solvent-nicotine solution for purposes of producing nicotine-loaded porous plugs.

The proper loading of nicotine from a solvent-nicotine solution into a porous polyolefin or polyolefindiene plug is not instantaneous. Thus to achieve the reproducability and uniformity desired for large-scale production of porous plugs containing a desired amount of nicotine, the average void volume for a latch of porous plugs was first determined. Then the plugs were exposed to a solvent-nicotine solution which has the desired amount of nicotine per plug contained in a plug void volume amount of solvent-nicotine solution.

After such exposure, excess solution was drained from the plugs, leaving each exposed plug with a "void volume" of solution contained largely therein in interstitial pores. The solvent was then evaporatively removed and the nicotine content of that "void volume" substantially absorbed by the porous plug. The conditions of temperature and pressure for evaporative removal of solvent were such that little nicotine was evaporatively removed therewith.

Yet other method variations are preferred to even further optimize the uniformity and reproduceability of nicotine loading by the processes of the present invention.

From a practical point of view, it has been found that porous polyolefin plugs exhibit a certain physical behavior upon exposure to solvents which affects the processes of the present invention. When porous plugs were mixed with solvent-nicotine solution in a container they fell into three categories: "settlers" which promptly subsided to the bottom of the container; "slowsettlers" which slowly subsided to the bottom of the container; and "floaters" which did not settle but floated near the solution surface. This behavior clearly indicated a range of apparent porous plug densities upon exposure to nicotine in a "wetting" solvent. This variation in density related to the degree of solution permeation into the labyrinthine pore structure of the plugs. As more fully described in Examples cited later herein, a more uniform permeation of the solution into the plugs was accomplished by very slow exposure of the plugs to the solution or even more clearly by incorporation of a vacuum degassing step.

A more uniform solution permeation resulted in a more uniform exposure of the plugs to the solution and, consequently, a preferred uniformity in nicotine loading into the plugs.

Thus the utilization of a vacuum degassing step in combination with the earlier described void volume determinations and nicotine-loading procedures based on void volume has been found as a highly preferred embodiment and "best mode" of the present invention.

The process by which porous polymeric plugs or items of the present invention may interact differently with a wetting solution is assumed to involve imperfections in the "wicking" or drawing-in of the solution by capillary action. Because of tortuous or labyrinthine patterns of porosity, quantities of air may become trapped and exclude solution. This air-trapping leads to plugs with differing apparent densities. A vacuum degassing step, as described earlier herein, eliminates these density variations and therefore the variations in solution-plug contact and nicotine loading.

The following examples are presented to illustrate aspects and embodiments of the present invention and are not intended to limit this invention except where otherwise indicated in the claims appended hereto.

EXAMPLE 1

Absorption of Nicotine Vapor by Various Polymers

Valox (polybutyleneterephthalate) in various forms was obtained from General Electric (Polymer Products Department). Tedlar (polyvinylfluoride film) was obtained from DuPont de Nemours & Company. Gafphite 1600A (polybutyleneterephthalate) was obtained from General Aniline Fiber. PPH (Polypropylene homopolymer) was obtained from Teel Plastics, Baraboo, Wis. Various preweighed samples (from 40 mg to about 800 mg in weight) of these polymers were incubated in sealed containers with a nicotine saturated air for different times and at different temperatures and again weighed. The results of these manipulations are shown in Table 1 and demonstrate that the polyolefin polypropylene may become loaded with nicotine from nicotine vapor.

TABLE 1

Percent Weight Gain For Various Polymers Subjected to Nicotine Vapors

| Sample | Temperature | Time (Days) | Weight Gain (wt. %) |
|---|---|---|---|
| Valox (10% glass filled) | ambient | 12 | 1.46 |
| Valox (10% glass filled) | 125° F. | 12 | 0.67 |
| Valox (40% glass filled) | ambient | 12 | 0.09 |
| Valox (40% glass filled) | 125° F. | 12 | 0.02 |
| Valox 310-083 | ambient | 7 | 0.08 |
| Valox 310-083 | 125° F. | 7 | 0.29 |
| Valox 310-095 | ambient | 7 | 0.10 |
| Valox 310-095 | 125° F. | 7 | 0.98 |
| Gafphite 1600A | ambient | 7 | 0.072 |
| Gafphite 1600A | 125° F. | 7 | 0.35 |
| Tedlar | ambient | 7 | 0.055 |
| Tedlar | 125° F. | 7 | 1.00 |
| PPH | 125° F. | 7 | 1.2 |
| PPH | 60° C. | 1 | 3.7 |
| PPH | 60° C. | 3 | 5.7 |
| PPH | 60° C. | 10 | 6.0 |
| PPH | 60° C. | 20 | 6.8 |
| PPH | 50° C. | 1 | 0.4 |
| PPH | 50° C. | 3 | 0.8 |
| PPH | 50° C. | 5 | 1.9 |
| PPH | 50° C. | 10 | 2.7 |
| PPH | 50° C. | 20 | 4.1 |
| PPH | 25° C. | 1 | 0.05 |
| PPH | 25° C. | 3 | 0.15 |
| PPH | 25° C. | 5 | 0.20 |
| PPH | 25° C. | 10 | 0.25 |
| PPH | 25° C. | 20 | 0.5 |
| PPH | 5° C. | 1 | 0.05 |
| PPH | 5° C. | 3 | 0.08 |
| PPH | 5° C. | 5 | 0.10 |
| PPH | 5° C. | 10 | 0.10 |
| PPH | 5° C. | 20 | 0.15 |

As the data in Table 1 indicates, under comparable conditions (polypropylene at 50° C. for 10 days and polybutylene terephthalate or polyvinylfluoride at 125° F. for 7 days), the polyolefin polypropylene is much more effective as a nicotine absorbent (2.7 wt. % gain) than is the polybutylene terephthalate (less than 1%) or polyvinyl fluoride (about 1%). Also, these results demonstrate the loading of polypropylene via vapor phase nicotine.

EXAMPLE 2

Polypropylene Absorption from Liquid Nicotine and Desorption Under Vacuum

Four polypropylene samples obtained from Teel, Baraboo, Wis., were washed, dried, weighed and immersed in liquid nicotine for 21 hours at 120° F. The samples were withdrawn, washed with water, dried and weighed again to determine the extent of nicotine absorption in the nicotine-loaded samples. These nicotine-loaded polypropylene samples were then placed in a vacuum desicator, subjected to a vacuum of about 75 mm of pressure for 10 min. and reweighed to determine loss of absorbed nicotine. The results of these manipulations are shown in Table 2.

TABLE 2

Polypropylene Absorption from Liquid Nicotine and Desorption Under Vacuum

| | 1 | 2 | 3 | 4 |
|---|---|---|---|---|
| Sample weight (mg) | 428.5 | 429.3 | 511.0 | 623.4 |
| Sample weight after immersion | 443.8 | 455.6 | 540.5 | 640.7 |
| Nicotine absorbed (mg) | 15.3 | 31.7 | 29.5 | 17.3 |
| % nicotine of sample weight | 3.6 | 7.5 | 5.8 | 2.8 |
| Sample weight after 10 min. under vacuum | 443.4 | 454.5 | 539.9 | 640.6 |
| Mg nicotine desorbed under vacuum | 0.4 | 1.1 | 0.6 | 0.1 |

As the above data indicate, polypropylene is an effective nicotine absorbent and that nicotine may be loaded into polypropylene by immersion in nicotine liquid.

EXAMPLE 3

Polyethylene Absorption of Vaporous Menthol

A low density polyethylene tube (8×84 mm) weighing 8.243 mg was sealed in a test tube with menthol crystals. The test tube was then placed in an oven at 125° F. for 2 hr. The tube was removed from the test tube, washed with ethanol, dried and weighed. The tube then weighed 865.4 mg, showing a weight increase of 41.1 mg ascribable to absorbed menthol. This experiment indicates that menthol, as well as nicotine may be absorbed by polyethylene and further demonstrates a loading of polyethylene by vapor phase menthol.

EXAMPLE 4

High Density Porous Polyethylene Absorption of Nicotine Vapors

Four samples (cylinders with about a ¼ inch diameter and 1½ inch length) of porous high density polyethylene were obtained from Porex Corp. (Fairburn, GA). These samples were weighed and then each incubated at ambient temperature in a sealed tube and in the presence of 40–50 mg nicotine. The weight of the samples were periodically determined and the resultant data shown in Table 3.

TABLE 3

Nicotine Weight Gain of Porous High Density Polyethylene

| | | Original Sample No. | | | |
|---|---|---|---|---|---|
| | | 1 | 2 | 3 | 4 |
| | | Weight (mg) | | | |
| | | 689.3 | 692.0 | 699.3 | 694.3 |
| Incubation | | Increase in weight (mg) | | | |
| Temp. | | ambient | ambient | 120° F. | 120° F. |
| Incubation | 1 hr | 1.0 | 1.0 | 3.5 | 4.2 |
| Time | 2 hr | 1.5 | 1.7 | 3.6 | 5.9 |
| | 1 day | 6.2 | 6.1 | 12.9 | 13.6 |
| | 6 days | 11.3 | | 17.7 | |

The data in Table 3 demonstrates the absorptive ability of high density porous polyethylene for nicotine vapors and the ability to load porous polyethylene plugs or items via nicotine vapors.

EXAMPLE 5

Vaporization of Nicotine from a Nicotine-Loaded Porous Polyethylene Plug

A 360 mg piece of Porex high density porous polyethylene was interposed in the passageway of an aluminum tube. The aluminum tube was 84 mm long, had an outer diameter of 5/16 inch and a wall thickness of 5/1000 inch. The porous plug was contacted with about 18 mg of liquid nicotine which was promptly absorbed to form a porous plug containing about 5% by weight nicotine. Thus loading a porous polyethylene plug by contact with a finite quarterly of nicotine is shown to be feasible loading method. Puffs of air (35 cc/puff) were drawn through the tube and nicotine-loaded porous plug at about 1050 cc per minute (2 sec/puff). The nicotine content of the air puffs was monitored by gas chromatography (Model 5880A, Hewlett Packard).

Table 4 contains data concerning nicotine in the air puffs.

TABLE 4

Nicotine Vaporized From A Porous Nicotine-Loaded Polyethylene Plug

| Time | Number Puffs | Micrograms Nicotine Per Puff |
|---|---|---|
| 10:31 | 1 | 8.2 |
| 10:33 | 74 | 8.1 |
| 10:36 | 147 | 6.7 |
| 10:40 | 220 | 5.6 |
| 10:43 | 292 | 5.2 |
| 10:46 | 365 | 4.7 |
| 10:49 | 438 | 4.2 |

TABLE 4-continued

Nicotine Vaporized From A Porous Nicotine-Loaded Polyethylene Plug

| Time | Number Puffs | Micrograms Nicotine Per Puff |
|---|---|---|
| 10:52 | 511 | 3.8 |
| 10:55 | 584 | 3.2 |
| 10:58 | 657 | 2.9 |

The total nicotine in the puffs was 3423 micrograms or about 19% of the nicotine originally loaded into the porous plug. The temperature was about 25° C. for these manipulations.

EXAMPLE 6

Loading Porous Plugs with Nicotine via a Solution Comprising Nicotine

Cylindrical porous polyethylene plugs (0.29 inches in diameter × 0.35 inches in length, weight about 160 mg) were obtained from Porex Corp., Fairburn Ga. and Chromex Corp., Brooklyn, N.Y. Such plugs were suitable for use in a nicotine dispenser with a cigarette shape. A sample of these porous plugs was wetted with a wetting solvent having relatively low volatility and known density, namely hexadecane. After draining the wetted porous plugs, their weight gain due to liquid held in pores by capillary action was used in calculations to determine the average plug void volume. This void volume primarily represents interconnected microscopic pores penetrated by the solvent. The particular void volume for the plugs used in this manipulation was 185 microliters per porous plug.

A solution of absolute ethanol with 5.4 weight percent nicotine was prepared. A mass of porous plugs was slowly covered with this solution and then drained so that each plug retained about 185 microliters (the void volume) of solution, representing about 10 mg nicotine. The drained plugs were transferred to a rotary vacuum drier and tumbled therein at a temperature of 50° C. and a vacuum of about 29 inches of mercury. The time for solvent evaporation varies according to the number of plugs present and design of the drier, but generally should be less than 3–4 hours. After the plugs were removed from the rotary vacuum drier, they were found to each contain about 10 mg nicotine.

EXAMPLE 7

Porous Polymeric Items, Density In A Solution And Loading Efficiency

Six groups of 100 cylindrical porous plugs (high density polyethylene) were obtained from Porex Corporation, Farburn, GA. Each plug weighted about 160 mg and was about 0.029 inches in diameter and about 0.35 inches in length. Each group of porous plugs was exposed in a different manner to a 5.4 weight percent nicotine solution in absolute ethanol. After exposure and the observation of density-related behavior of the plugs in the solution, the plugs were drained and dried as described in Example 6. The extent of nicotine incorporated into the plugs was estimated by weighing.

Table 5 contains data concerning these manipulations and observations.

TABLE 5

Variations in Nicotine-Loading Methods

| Group No. | Treatment | Visual Observations of Behavior in Solution | Nicotine as (% Maximum Load) |
|---|---|---|---|
| (1) | Porous itmes dropped into solution | about 10% "floaters"* and many "slowsetters"* | not determined |
| (2) | Porous plugs placed in container, solution slowly introduced from bottom | about 5% "floaters" about 10–15% "slow-settlers" | about 95% |
| (3) | Solution added to items, container evacuated until air bubbles cease and solvent boiling just begins. Vacuum then released. | no "floaters" a few "slowsettlers" | 98.5% |
| (4) | As with No. 3, but repeat process once | no "floaters" no "slowsettlers" | 100% |
| (5) | Establish vacuum over dry items, introduce solution into vaccum. | no "floaters" no "slowsettlers" | 98.5% |
| (6) | As with No. 5, but re-establish fresh vacuum after introduction of solution. | no "floaters" no "slowsettlers" | 100% |

*"Floaters" are those items which float near the surface of the solution for at least a 1–5 minute period. "Slowsettlers" are those plugs noticeably slower than most plugs in their sinking behavior. As may be seen by an examinationer of the observations and data in Table 5, the foating or slowsettling behavior correlates with decreased nicotine loading on the average. Less than maximal loading represents a mixture of partially nicotine-loaded plugs and fully nicotine-loaded plugs. Thus, in the preferred embodiment of the present invention the process of deassing is important to achieve an optimally uniform and reproduceable nicotine-load.

Changes may be made in the construction, operation and arrangement of the various parts, elements, steps and procedures described herein without departing from the concept and scope of the invention as defined in the following claims.

What is claimed is:

1. A method of producing porous polyethylene or polypropylene items loaded with nicotine, the method comprising:
   emplacing said items and nicotine in a vessel wherein said nicotine comes into contact with said items;
   closing said vessel for a period of time; and
   removing said items loaded with nicotine from the vessel.

2. The method of claim 1 wherein the polyolefin or polyolefindiene is polyethylene, polypropylene, poly-butadiene, poly-1-butene, polyisobutylene, polyisoprene, poly-4-methyl-1-pentene or combinations thereof.

3. The method of claim 1 wherein the polyethylene or polypropylene is polyethylene.

4. The method of claim 1 wherein the nicotine in the vessel is nicotine liquid.

5. The method of claim 1 wherein the nicotine in the vessel is nicotine vapor.

6. The method of claim 1 wherein the nicotine in the vessel is included in a solution with a fluid solvent, the fluid solvent having adherence for polyethylene or polypropylene surfaces.

7. The method of claim 6 where the solution comprises between about 1% and about 10% nicotine.

8. A method of producing porous polyolefin items loaded with nicotine, the method comprising:
   emplacing the porous polyolefin items in a vessel;
   preparing a solution comprising between about 1% nicotine and about 10% nicotine and a fluid solvent for nicotine, the fluid solvent demonstrating an adherence to polyolefin surfaces;
   adding to the vessel a quantity of the solution sufficient to contact at least a majority of the polyolefin items;
   draining excess solution from the items; and
   evaporating solvent from the drained items to produce porous polyolefin items loaded with nicotine.

9. The method of claim 8 wherein the porous polymeric items consist essentially of polyethylene or polypropylene.

10. The method of claim 8 wherein the porous polymeric items consist essentially of polyethylene.

11. The method of claim 8 or 1 wherein the nicotine is d-nicotine, l-nicotine or dl-nicotine.

12. The method of claim 8 wherein the polyolefin is polyethylene or polypropylene.

13. The method of claim 8 wherein the polyolefin is polyethylene.

14. The method of claim 8 wherein the solvent demonstrating an adherence to a polyolefin surface and has a boiling point less than about 200° C.

15. The method of claim 8 wherein the porous polyolefin items are porous plugs suitable for use in a nicotine dispenser with a cigarette shape.

16. The method of claim 15 wherein a void volume of the plugs is determined by observing the amount of a wetting solvent retained by said plugs.

17. The method of claim 16 wherein a desired amount of nicotine per plug is determined by preparing a nicotine solution so that the desired amount of nicotine per plug is contained in a volume of the solution about equal to the void volume of a plug.

18. The method of claim 17 wherein the desired amount of nicotine per plug is about 10 mg and the solution comprises about 5.4 weight percent nicotine.

19. The method of claim 8 wherein, immediately after the adding step, a step is added comprising:
   partially evacuating the vessel to substantially degas the porous polymeric items.

20. A method of producing porous polyolefin items loaded with nicotine, the method comprising:

contacting porous polyolefin items with a solution comprising a solvent for nicotine and between about 1% nicotine and about 10% nicotine, the solvent having a boiling point below about 200° C. and an adherence for polyolefin surfaces;
draining excess solution from the items; and
evaporating solvent from the drained items to produce polyolefin items loaded with nicotine.

21. A method of loading nicotine into porous polyolefin items, the method comprising:
immerging porous polyolefin items in a solution comprising a solvent for nicotine and between about 1% nicotine and about 10% nicotine, the solvent having a boiling point below about 200° C. and having adherence for polyolefin surfaces;
exposing said immerged items at least once to a partial vacuum to degas said items;
draining excess solution from the items; and
evaporating solvent from the drained items to produce porous polyolefin items loaded with nicotine.

22. The method of claim 20 or 21 wherein the porous polyolefin items comprise polyethylene and the solvent consists essentially of ethanol.

23. A method of loading nicotine into porous polymeric items consisting essentially of a polyolefin or polyolefindiene, the method comprising: contacting said items with liquid nicotine in a closed vessel.

24. A method of loading nicotine into porous polymeric items consisting essentially of a polyolefin or polyolefindiene, the method comprising: contacting said items with a solution comprising nicotine and a fluid solvent with adherence for a polyolefin or polyolefindiene surface.

25. The method of claim 24 wherein the solution comprises between about 1% and about 10% nicotine.

26. The method of claim 24 wherein the additional steps are added of:
draining excess solution from the items; and
evaporating fluid solvent from the drained items.

27. The method of claim 8, 24 or 6 wherein the fluid solvent is an alkyl alcohol with between one and eight carbon atoms, a paraffin or olefin with between one and six carbon atoms, a ketone with between three and eight carbon atoms, an aliphatic ether with between two and six carbon atoms, an aliphatic ester with between four and six carbon atoms, liquid $CO_2$, or halogenated paraffins having between one and six carbon atoms.

28. The method of claim 8, 24 or 6 wherein the fluid solvent consists essentially of methanol, ethanol, propanol, isopropanol or a mixture thereof.

29. The method of claim 8, 24 or 6 wherein the solvent consists essentially of ethanol.

30. The method of claim 23, 1 or 8 wherein the nicotine is accompanied by an anti-oxidant.

31. The method of claim 30 wherein the anti-oxidant is butylated hydroxyanisole, butylated hydroxytoluene, propyl gallate or tertiary butyl hydroxyquinone.

32. The method of claim 23, 1 or 8 wherein the nicotine is accompanied by a flavorant.

33. The method of claim 32 wherein the flavorant is menthol, tobacco extract or a mixture thereof.

34. The method of claim 8, 24 or 6 wherein the fluid solvent is supercritical fluid $CO_2$, $N_2$ or $NH_3$.

35. The method of claim 8, 24 or 6 wherein the fluid solvent is liquid $CO_2$.

* * * * *